United States Patent [19]

Amundsen et al.

[11] Patent Number: 4,783,482

[45] Date of Patent: Nov. 8, 1988

[54] BIS(THIOCYANATO)PALLADIUM(II)COMPLEXES

[75] Inventors: Alan R. Amundsen, Somerville; Eric W. Stern, Mountainside, both of N.J.

[73] Assignee: Engelhard Corporation, Edison, N.J.

[21] Appl. No.: 798,034

[22] Filed: Nov. 14, 1985

Related U.S. Application Data

[60] Division of Ser. No. 642,315, Aug. 20, 1984, Pat. No. 4,578,491, which is a continuation of Ser. No. 392,816, Jun. 28, 1982, abandoned.

[51] Int. Cl.$^4$ .................... A61K 31/28; A61K 31/555
[52] U.S. Cl. .................................. 514/492; 514/184
[58] Field of Search .............................. 514/184, 442

Primary Examiner—Jerome D. Goldberg

[57] ABSTRACT

There are described novel bis(thiocyanato)palladium-(II) complexes containing bidentate amine ligands. These complexes exhibit an anti-tumor effect against malignant animal tumor cells sensitive thereto and are characterized by low mammalian toxicity.

19 Claims, No Drawings

BIS(THIOCYANATO)PALLADIUM(II)COMPLEXES

This is a division of application Ser. No. 642,315 filed Aug. 20, 1984, now U.S. Pat. No. 4,578,491, which is a continuation of application Ser. No. 392,816, filed June 28, 1982, now abandoned.

This invention relates to a novel class of bis(thiocyanato) palladium compounds, pharmaceutical compositions comprising same and a method for the treatment malignant animal tumor cells sensitive thereto via the administration of said compositions.

There are very few palladium complexes which are useful in the treatment of malignant animal tumor cells.

It is an object of this invention to add to the known family of precious metal-containing anti-tumor agents by providing a new and rationally developed class of palladium complexes.

BACKGROUND

Certain platinum complexes are active against tumors and this discovery has spawned a renewed interest in metal complexes in general as a source of anti-cancer agents. Cisplatin, cis-[Pt(NH$_3$)$_2$Cl$_2$], for example, has been singularly successful in bringing about a regression of testicular and ovarian tumors and, as a result, other platinum derivatives have been investigated for anti-tumor activity.

These developments have led to the exploitation of structure-activity relationships, including the synthesis of various palladium analogs; however, most palladium analogs have failed to show any discernable activity, and the activity which has been observed is of a very low order. Speculation has it that the palladium(II) amine complexes are extremely reactive and this liability causes them to react with other molecules in vivo prior to reaching the cancer which is sought to be treated (M. J. Cleare and J. D. Hoeschele; Bioinorganic Chemistry, Vol. 2: page 187 (1973); and M. J. Cleare; Coordination Chemistry Reviews, Vol. 12: page 349 (1973)). Accordingly, it has been impossible heretofore to develop a class of palladium compounds which parallel the known platinum-containing anti-tumor agents.

THE INVENTION

This invention relates to a novel class animal of palladium complexes which are useful as anti-tumor agents against tumor cells.

Specifically, this invention relates to bis(thiocyanato) palladium(II) complexes which contain bidentate amine ligands in a 5-membered chelate ring. These compounds exhibit excellent activity against malignant animal tumor cells sensitive thereto in animals, and they provide a higher order of activity and a lower dose-limiting toxicity than is possible with other known palladiun analogs.

The structure of the present compounds is unique and critical. Related analogs having 6- and 7-membered chelate rings are inactive as anti-tumor agents and palladium analogs coordinated with groups other than thiocyanato (SCN$^-$) have also been shown to be essentially inactive in inhibiting the growth of S180 ascites. By contrast, the products of the present invention, administered in therapeutic dosages and conventional vehicles bring about a regression of S180 ascites in mammals and otherwise ameliorate conditions associated with tumor activity.

The products of this invention are compounds of the following formula:

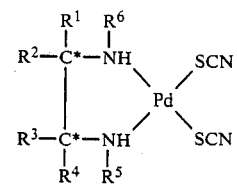

wherein $R^1$ and $R^4$ are selected from the group consisting of hydrogen and lower alkyl; $R^2$ and $R^3$ are selected from the group consisting of hydrogen, C$_{1-6}$ alkyl, hydroxymethyl or, taken together, $R^2$ and $R^3$ represent C$_{2-6}$ alkylene; $R^1$-$R^4$, taken together with the carbon atoms to which they are attached, represent naphthylene or a phenylene of the formula:

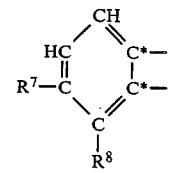

wherein $R^7$ and $R^8$ represent hydrogen, C$_{1-6}$ alkyl, hydroxy or carboxy; and $R^5$ and $R^6$ are selected from the group consisting of hydrogen, C$_{1-6}$ alkyl, hydroxymethyl or carboxymethyl.

A preferred emboidment of this invention relates to products of the formula:

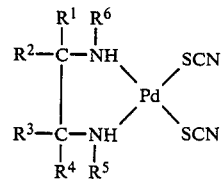

wherein $R^1$ and $R^4$ represent hydrogen; $R^2$ and $R^3$ are selected from the group consisting of hydrogen, C$_{1-6}$ alkyl or, taken together, $R^2$ and $R^3$ represent C$_{1-6}$ alkyl containing from about 3-5 carbon atoms; $R^1$-$R^4$, taken together with the carbon atoms to which they are attached, represent a phenylene of the formula:

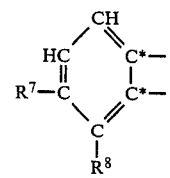

wherein $R^7$ and $R^8$ represent hydrogen or C$_{1-6}$ alkyl; and $R^5$ and $R^6$ are selected from the group consisting of hydrogen and C$_{1-6}$ alykl. This embodiment or class of products exhibits predictably good anti-tumor activity against malignant animal tumor cells sensitive thereto and constitutes a preferred subgroup of compounds within the scope of this invention.

PHARMACOLOGY

The products of this invention are useful in the treatment of malignant animal tumor cells sensitive thereto in animals as, for example, Sarcoma 180 ascites tumor cells in animals such as mice. This anti-tumor cell effect also may extend to other sarcomas and to such other tumors as the following: lymphoid leukemia, lymphosarcoma, myelocytic leukemia, malignant lymphona, squamous cell carcinoma, adenocarcinoma, scirrhous carcinoma, malignant melanoma, seminoma, teratoma, choriocarcinoma, embryonalcarcinoma, cystadenocarcinoma, endometrioidcarcinoma or neuorblastoma and the like. In addition, said complexes may be useful as anti-viral, anti-inflammatory, anti-bacterial and anti-parasitic agents.

They may be administered parenterally or orally in admixture with a non-toxic pharmacologically acceptable inert carrier or diluent in any of the usual pharmaceutical forms. These include solid and liquid oral unit dosage forms, such as tablets, capsules, powders and suspensions or solutions and suspensions for subcutaneous, intramuscular, intravenous or intra-arterial injection.

The term "unit dosage" refers to physically discrete units which may be administered in single or multiple dosages each containing a predetermined quantity of the active ingredient in association with the required diluent, carrier or vehicle. The quantity of active ingredient is the amount of the complex which is needed to produce the desired therapeutic effect.

A typical unit dosage consists essentially of from about 5 to 400 mg. of active ingredient; however, the form in which said ingredient is administered and the frequency of administration is usually determinative of the concentration. Thus, for example, oral unit dosage forms containng 5 to 400 mg. of active ingredient may be administered one or more times per day, depending upon the severity of the tumor cells which is sought to be treated and the condition of the host animal. By contrast, parenteral administration generally requires from about 20 to 200 mg. of the active ingredient per unit dosage administered as a daily dose or as a fraction thereof, depending upon whether the regimen calls for adminstration once, twice, three or four times daily.

By contrast to the "unit dosage", the effective dose is that dosage which is needed to achieve the desired anti-tumor effect against malignant animal tumore cells sensitive thereto. In general, this dosage lies within the range of from about 3 to 960 mg. of the active ingredient per kg. of body weight of the host animal. A preferred concentration lies within the range of from about 10 to 160 mg./kg. of body weight. For oral administration it has been found that an effective dose of 15 to 960 mg./kg. is most suitable, whereas in the case of parenteral administration, it is usually advisable to employ from about 3 to 160 mg./kg. These dosages are well below the toxic or lethal dose, and they may be varied over a wide range for adjustment to the aniaml which is being treated.

In this invention, the term "pharmacologically acceptable inert carrier or diluent" denotes a non-toxic substance which, when mixed with the active ingredient, renders it more suitable for adminstration. Compositions intended for oral administration may include such carriers or diluents as corn starch, potato starch, sodium carboxymethyl cellulose, ethyl cellulose, cellulose acetate, powdered gum tragacanth, gelatin, alginic acid, agar, stearic acid or the sodiuum, calcium and magnesium salts of stearic acid, sodium lauryl sulfate, polyvinynlpyrrolidone, sodium citrate, calcium carbonate and dicalcium phosphate. Said compositions may also contain non-toxic adjuvants and modifiers, such as dyes, buffering agents, preservatives, surfactants, emulsifers, flavoring agents or biocides and the like.

Tablets are prepared by mixing a complex of this invention in a suitably comminuted or powdered form with a diluent or base such as starch, kaolin, di-calcium phosphate and the like. The resulting mixture can be granulated by wetting with a binder, such as a syrup, starch (paste), acacia mucilage or solutions of cellulosic or polymeric materials, whereafter the wetted mixture is forced through a screen. As an alternative to granulating, the powdered mixture can be run through a tablet machine and imperfectly formed slugs broken into granules. The granules are lubricated to prevent sticking to the tablet-forming dies via the addition of stearic acid, a stearate salt, talc or mineral oil and the lubricated mixture is then compressed into tablets. The complexes can also be combined with free-flowing inert carriers followed by compression into tablets, without going through the granulating or slugging steps. A protective coating or sealing coat of shellac, sugar or polymeric material and a polished coating of wax can also be provided. Dyestuffs may be added to distinguish different unit dosages.

Capsules are formulated by preparing a powdered mixture, according to the procedure hereinbefore described and pouring said mixture into preformed gelatin sheaths. A lubricant such as talc, magnesium stearate or calcium stearate can be added as an adjuvant prior to the filling operation. A glidant such as colloidal silica may be added to improve the flow characteristics and a disintegrating or solubilizing agent may also be added to enhance the effectiveness of the medicament upon ingestion.

Powders are prepared by comminuting the compound to a fine size and mixing with a similarly comminuted pharmaceutical diluent or carrier, such as an edible carbohydrate as, for example, starch. Sweetening agents and flavorings, preservatives and dispersing and/or coloring agents may also be employed.

Oral fluids such as syrups and elixirs are prepared in unit dosage form so that a given quantity of medicament, such as a teaspoonful, will contain a predetermined amount of the active ingredient. Suspensions can be formulated by dispersing the active ingredient in a non-toxic vehicle in which it is essentially insoluble.

Fluid unit dosage forms for parenteral administration can be prepared by placing a measured amount of the complex in an ampoule or vial which is sterilized and sealed. An accompanying vial or vehicle can be provided for mixing with said complex prior to administration.

This invention also provides for combining two or more of the subject complexes into a single unit dosage form or, alternatively, combining one or more of said complexes with other known anti-tumor agents against malignant animal tumore cells sensitive thereto, therapeutic agents or nutritive agents and the like, so as to enhance or complement the antitumor effect.

The preferred compositions for oral administration are tablets in which the thiocyanate complex is present in quantities of about 60 to 400 mg. but, preferably, 125 to 300 mg. in a pharmaceutically acceptable, orally ingestible solid carrier. If desired, the composition may also contain flavors, binders, lubricants and other excipients known in the art.

A preferred alternative for oral administration is the soft gelatin capsule. Such a composition may contain from about 60 to 400 mg. but, preferably, 125 to 350 mg. by weight of active ingredient dissolved or suspended in vegetable oil, peanut oil, alcohol or glycerine and the like.

The following embodiments illustrate representative unit dosage forms.

Compressed Tablet

A tablet suitable for swallowing is prepared by mixing the following ingredients:

| | |
|---|---|
| Bis(Thiocyanato)-1,2-Di-aminocyclohexanepalladium(II) | 250 mg. |
| Niacinamide | 50 mg. |
| Calcium Pantothenate | 20 mg. |
| Magnesium Sulfate | 50 mg. |
| Zinc Sulfate | 50 mg. |
| Magnesium Stearate | 10 mg. |
| | 430 mg. |

The bis(thiocyanato)-1,2-diaminocyclohexanepalladium(II), niacinamide, calcium pantothenate, magnesium sulfate, zinc sulfate and magnesium stearate (5.0 mg.) are mixed and compressed into slugs. The slugs are then broken into granules and sifted through an 8 mesh screen. Additional magnesium stearate (5.0 mg.) is added and the mixture is then compressed into tablets suitable for oral administration.

Soft Gelatin Capsule

A soft elastic gelatin capsule is filled with the following ingredients:

| | |
|---|---|
| Bis(Thiocyanato)-1,2-Di-aminocyclohexanepalladium(II) | 150 mg. |
| Wheat germ oil | 50 mg. |
| Sunflower seed oil | 100 mg. |
| | 300 mg. |

The bis(thiocyanato)-1,2-diaminocyclohexanepalladium(II) and wheat germ oil are mixed with sunflower seed oil and the resulting mixture is poured into gelatin capsules suitable for oral administration. An alternative embodiment provides for substituting sunflower seed oil and wheat germ oil with equal amounts of peanut oil to obtain an otherwise similar capsule which is also suitable for oral administration.

Dry-Filled Capsule

A hard dry-filled capsule may be prepared from the following ingredients:

| | |
|---|---|
| Bis(Thiocyanato)-o-Phenylene-diaminepalladium(II) | 300 mg. |
| Niacinamide | 50 mg. |
| Calcium Pantothenate | 10 mg. |
| | 360 mg. |

The bis(thiocyanato)-o-phenylenediaminepalladium(II) is reduced to a No. 60 powder. Niacinamide and calcium pantothenate are passed through a No. 60 bolting cloth and these ingredients are added to the bis(thiocyanato)-o-phenylenediaminepalladium(II). This combination of ingredients is mixed for 10 minutes and then poured into a No. 3 size gelatin capsule.

Dry Powder

The following composition illustrates a representative dosage in dry powder form. In this embodiment, the active ingredient is combined with up to 75% by weight of a suitable flavoring agent. All quantities are in a weight-percent relationship.

| | |
|---|---|
| Bis(Thiocyanato)ethylene-diaminepalladium(II) | 25–90% |
| Flavoring Agent | 10–75% |
| Preservative | 0–1.0% |

The bis(thiocyanato)-ethylenediaminepalladium(II), flavoring agent and preservative are thoroughly blended to afford a homogenous dry powder. The resulting formulation may be blended with other therapeutic agents to afford combination-type medicinals. Alternatively, said powder may be dissolved in a pharmacologically acceptable diluent to afford a solution which is suitable for oral administration.

Compositions intended for parenteral administration may include such diluents and carriers as water-miscible solvents as, for example, sesame oil, groundnut oil, and aqueous propylene glycol. Typical of said compositions are solutions which contain the active ingredient in sterile form. An embodiment illustrating a dosage form suitable for intravenous injection is set forth below.

Parenteral Solution

Injectable solutions can be formulated by mixing an ampoule of active ingredient with an ampoule of sterile diluent:

| | |
|---|---|
| Ampoule: Bis(Thiocyanato)ethylene-diaminepalladium(II) | 300 mg. |
| Ampoule: Sterile Water (Diluent for Injection) | 2 cc. |

The bis(thiocyanato)ethylenediaminepalladium(II) and water are mixed thoroughly immediately prior to adminstration. If desired, one or more other active ingredients may be added to provide an injectable solution having enhanced therapeutic activity.

PREPARATIVE METHODS

The products of this invention are prepared by treating a palladium salt with a metal thiocyanate to afford in solution the $Pd(SCN)_4^{-2}$ anion. This intermediate is then treated with ethylenediamine or a derivative of said diamine to yield the desired product (I, infra). The palladium salts are highly reactive compounds, and they are characterized by substituents which ultimately are displaced by the thiocyanato radical ($SCN^-$). Typical of said salts are, for example, palladium halide and alkali metal tetrahalopalladate:

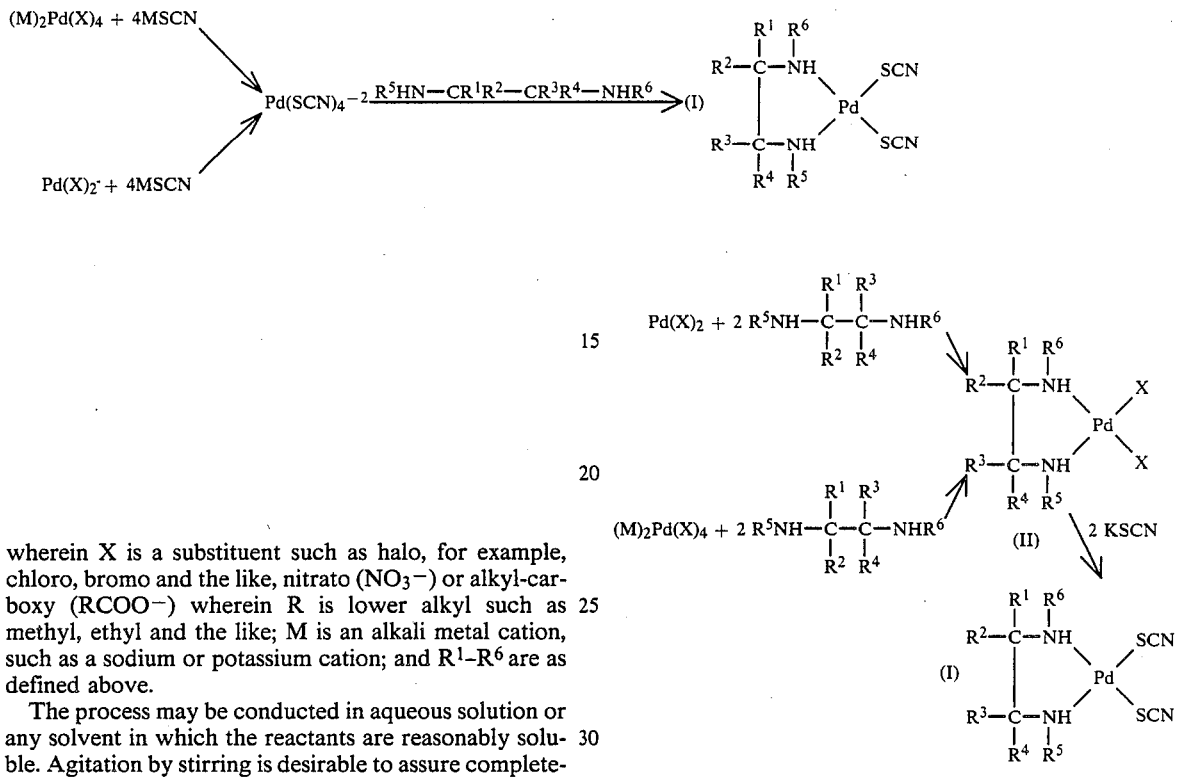

wherein X is a substituent such as halo, for example, chloro, bromo and the like, nitrato ($NO_3^-$) or alkyl-carboxy ($RCOO^-$) wherein R is lower alkyl such as methyl, ethyl and the like; M is an alkali metal cation, such as a sodium or potassium cation; and $R^1$-$R^6$ are as defined above.

The process may be conducted in aqueous solution or any solvent in which the reactants are reasonably soluble. Agitation by stirring is desirable to assure completeness of the reaction, and stirring is continued until the thiocyanate reactant has dissolved, whereupon, the diamine reactant is added and the mixture is stirred again at room temperature.

The high reactivity of the palladium salts assures a rapid reaction with the thiocyanate reactant; however, a complete reaction with the diamine may require a period of several hours.

Temperature is not critical and, therefore, ambient temperatures may be employed with good results; however, it may be desirable in some instances to facilitate the process by using temperatures in the range of from about 0° to 70° C.

The reactants are generally employed in stoichiometric amounts; therefore, in the first stage 4 moles of thiocyanate reactant should be present per mole of palladium salt, whereas in the second stage, the $Pd(SCN)_4^{-2}$ and diamine reactant should be present in essentially equal molar quantities.

The process is ordinarily conducted in an aqueous medium but alcoholic solutions, such as methanol or ethanol, also may be employed. The products are obtained from solution in the form of precipitates which may be isolated by filtration and then washed and dried. Recrystallization from water or alcohol yields a purified product.

A modification of the aforedescribed method consists of treating the $M_2PdX_4$ or $PdX_2$ in solution with MSCN to afford bis(thiocyanato)palladium(II) [$Pd(SCN)_2$]. This intermediate can be isolated for use as a starting material in the reaction with the ethylenediamine reactant. In this method, the bis(thiocyanto)palladium(II) is converted to the final product (I) in a single step.

An alternative method consists of first treating the palladium salt with the diamine reactant, followed by the reaction of the resulting intermediate (II, infra) with a metal thiocyanate:

wherein M, X and $R^1$-$R^6$ are as defined above. The products (I) thus obtained are essentially insoluble in water at room temperature.

The following examples illustrate the methods by which the products (I) of this invention are obtained, the use of such products, as well as comparative products which were found to be inactive. All parts and percents are by weight, unless otherwise specified.

EXAMPLE 1

Bis(Thiocyanato)ethylenediaminepalladium(II)

Sodium tetrachloropalladate (1.47 g, 5 mmoles) was dissolved in water (50 ml) and solid potassium thiocyanate (1.95 g, 20 mmoles) was added. The mixture was stirred until all of the potassium thyiocyanate dissolved and a dark red solution formed. To this solution was added, in portion, a solution of ethylenediamine (0.3 g, 5 mmoles). A yellow-orange precipitate formed immediately and the mixture was stirred for 10 minutes, cooled to 0° C. and filtered. The precipitate was washed with cold water and vacuum dried to afford 1.14 g (80.7%) of bis-(thiocyanato)ethylenediaminepalladium-(II).

The elemental analysis for this product is set forth below.

| | Analysis for $PdC_4H_8N_4S_2$: | | | |
|---|---|---|---|---|
| | % Pd | % C | % H | % N |
| Calculated: | 37.64 | 17.00 | 2.85 | 19.82 |
| Found: | 36.24 | 17.77 | 2.43 | 20.68 |

The infrared spectrum for bis(thiocyanato)ethylenediaminepalladium(II) showed a band at 2100 $cm^{-1}$, assigned to $\nu_{CN}$; a band at 425 $cm^{-1}$, assigned to $\delta_{NCN}$; and a band at 700 $cm^{-1}$, assigned to $\nu_{CS}$.

EXAMPLE 2

Bis(Thiocyanato)-1,2-Diaminopropanepalladium(II)

The procedure of Example 1 was repeated, except that 1,2-diaminopropane was substituted for ethylenediamine in an otherwise similar reaction. There was thus obtained a 75.9% yield of bis(thiocyanato)-1,2-diaminopropanepalladium(II). Palladium analysis for $PdC_5H_{10}N_4S_2$: Calculated, 35.86%; Found, 35.01%.

The infrared spectrum for this product showed a band at 2105 cm$^{-1}$, assigned to $\nu_{CN}$; a band at 435 cm$^{-1}$, assigned to $\nu_{NCN}$; and a band at 715 cm$^{-1}$, assigned to $\nu_{CS}$.

EXAMPLE 3

Bis(ThiocYanato)-1,2-Diaminocyclohexanepalladium-(II)

Palladium chloride (1.77 g, 10 mmoles) was suspended in a solution of potassium thiocyanate (4.85 g, 40 mmoles) in water (30 ml) and this mixture was stirred at room temperature for one hour. A dark red solution was obtained. Ethanol (30 ml) was added followed by the slow addition of 1,2-diaminocyclohexane (1.14 g, 10 mmoles) dissolved in a mixture of water (5 ml) and ethanol (5 ml). A fine yellow-orange precipitate and a brown oil formed immedietely, and after the oil settled the suspension was decanted. Ethanol (25 ml) was added and the mixture was cooled overnight in a refrigerator. The product was filtered, washed with cold water and vacuum dried to afford 0.82 g (24.4%) of bis(thiocyanato)-1,2-diaminocyclohexane-palladium-(II).

| Analysis for $PdC_8H_{14}N_4S_2$: | | | |
|---|---|---|---|
| | % C | % H | % N |
| Calculated: | 28.53 | 4.19 | 16.64 |
| Found: | 30.57 | 3.94 | 17.54 |

The infrared spectrum for this product showed a band at 2110 cm$^{-1}$, assigned to $\nu_{CN}$; a band at 410 cm$^{-1}$, assigned to $\nu_{NCN}$; and a band at 710 cm$^{-1}$, assigned to $\nu_{CS}$.

EXAMPLE 4

Bis(Thiocyanato)-N,N'-Dimethylethylenediaminepalladium(II)

Sodium tetrachloropalladate (0.588 g, 2 mmoles) was dissolved in water (10 ml) and solid potassium thiocyanate (0.777 g, 8 mmoles) was added, followed by stirring over a five minute period. A red solution formed and to this mixture was added N,N'-dimethylethylenediamine (0.176 g, 2 mmoles) in water (5 ml). A red oil formed immediately and it was dissolved by the addition of ethanol (10 ml). The mixture was stirred for 15 minutes at room temperature and the solvent was removed under vacuum at 50° C. The remaining oil was dissolved in a mixture of water (10 ml). After having been stored in a freezer overnight, additional water (50 ml) was added. The mixture was again placed in the freezer, this time for 48 hours. There was thus obtained an orange product which was filtered, washed with water and vacuum dried to afford 0.18 g (28.9%) of bis(thiocyanato)-N,N'-dimethylethylenediaminepalladium(II). Palladium analysis for $PdC_6H_{12}N_4S_2$: Calculated, 34.02%; Found, 33.67%.

The infrared spectrum for this product showed a band at 2100 cm$^{-1}$, assigned to $\nu_{CN}$; a band at 415 cm$^{-1}$, assigned to $\nu_{NCN}$; and a band at 710 cm$^{-}$, assigned to $\nu_{CS}$.

EXAMPLE 5

Bis(Thiocyanato)-o-Phenylenediaminepalladium(II)

Sodium tetrachloropalladate (1.47 g, 5 mmoles) was dissolved in water (25 ml) and solid potassium thiocyanate (1.94 g, 20 mmoles) was added. The mixture was stirred for 5 minutes and solid o-phenylenediamine (0.54 g, 5 mmoles) was added to the resulting dark red solution. The resulting mixture was stirred at room temperature for two hours during which time the color of the solid changed to yellow. The product was filtered, washed with three 10 ml portions of water and vacuum dried. The yield of bis(thiocyanato)-o-phenylenediaminepalladium(II) was 1.54 g (93.1%). Palladium analysis for $PdC_8H_8N_4S_2$: Calculated, 32.17%; Found 30.47%.

The infrared spectrum for this product showed a band at 2100 cm$^{-1}$, assigned to $\nu_{CN}$; a band at 425 cm$^{-1}$, assigned to $\nu_{NCN}$; and a band at 700 cm$^{-1}$, assigned to $\nu_{CS}$.

EXAMPLE 6

Bis(Thiocyanato)-4,5-Dimethyl-o-Phenylenediaminepalladium(II)

The procedure of Example 5 was repeated, except that 4,5-dimethyl-o-phenylenediamine was substituted for o-phenylenediamine, and the mixture was stirred for 24 hours. There was thus obtained 86.41% of bis(thiocyanato)-4,5-dimethyl-o-phenylenediaminepalladium(II). Palladium analysis: Calculated, 29.55%; Found, 28.56%.

The infrared spectrum for this product showed a band at 2110 cm$^{-1}$, assigned to $\nu_{CN}$; a band at 430 cm$^{-1}$, assigned to $\nu_{NCN}$; and a band at 710 cm$^{-1}$, assigned to $\nu_{CS}$.

EXAMPLES 7-19

The procedure of Example 1 was repeated using a substituted diamine in lieu of the ethylenediamine therein described. The following equation and accompanying table illustrate this method, the starting materials employed and the final products obtained thereby:

$$NaPdCl_4 + 4KSCN \longrightarrow Pd(SCN)_4^{-2}$$

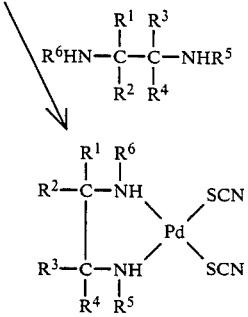

TABLE 1

| Ex. | R¹ | R² | R³ | R⁴ | R⁵ | R⁶ |
|---|---|---|---|---|---|---|
| 7 | H | —CH₂—CH₂—CH₂— | | H | H | H |
| 8 | H | —CH₂—(CH₂)₃—CH₂— | | H | H | H |
| 9 | — | =CH—CH=C(CH₃)—CH= | — | | H | H |
| 10 | — | =CH—CH=C(COOH)—CH= | — | | H | H |
| 11 | — | =CH—CH=C(OH)—CH= | — | | H | H |
| 12 | — | =CH—C≡C—CH= / HC CH \\ CH—CH // | — | | H | H |
| 13 | H | —CH₃ | —CH₃ | H | H | H |
| 14 | H | —CH₂OH | —CH₂OH | H | H | H |
| 15 | H | —CH₃ | —CH₂CH₃ | H | H | H |
| 16 | H | —CH₂OH | —CH₃ | H | H | H |
| 17 | H | H | H | H | —CH₂COOH | —CH₂COOH |
| 18 | H | H | H | H | —CH₂OH | —CH₂OH |
| 19 | H | —CH₃ | —CH₃ | —CH₃ | H | H |

COMPARATIVE EXAMPLES A–C

The procedure of Example 1 was repeated, except that 1,3-diaminopropane, 1,4-diaminobutane and 1,3-diamino-2propanol were substituted for ethylenediamine to afford, respectively: bis(thiocyanato)-1,3-diaminopropanepalladium(II), bis(thiocyanato)-1,4-diaminobutanepalladium(II) and bis(thiocyanato)-1,3-diamino-2-propanolpalladium(II).

The bis(thiocyanato)1,3-diaminopropanepalladium-(II) was obtained in a 44.5% yield. The infrared spectrum for this product showed a band at 2095 cm⁻¹, assigned to $\nu_{CN}$; a band at 410 cm⁻¹, assigned to $\nu_{NCN}$; and a band at 710 cm⁻¹, assigned to $\nu_{CS}$. Palladium analysis: Calculated, 35.86%; Found, 35.88%.

The bis(thiocyanato)-1,4-diaminobutanepalladium(II) was obtained in a 78.9% yield. The infrared spectrum for this product showed a band at 2095 cm⁻¹, assigned to $\nu_{CN}$; a band at 415 cm⁻¹, assigned to $\delta_{NCN}$; and a band at 710 cm⁻¹, assigned to $\nu_{CS}$. Palladium analysis: Calculated, 34.24%; Found, 31.87%.

The bis(thiocyanato)-1,3-diamino-2-propanolpalladium(II) was obtained in a 73.6% yield. The infrared spectrum for this product showed a band at 2100 cm⁻¹, assigned to $\nu_{CN}$; a band at 420 cm⁻¹, assigned to $\delta_{NCN}$; and a band at 715 cm⁻¹, assigned to $\nu_{CS}$. Palladium analysis: Calculated, 33.97%; Found, 32.80%.

COMPARATIVE EXAMPLE D

The procedure of Example 5 was used to produce bis(thiocyanato)-1,8-diaminonaphthalenepalladium(II). In this method, 1,8-diaminonaphthalene was substituted for the o-phenylenediamine of Example 5 and the reaction mixture was stirred for 48 hours instead of two hours. There was thus obtained bis(thiocyanato)-1,8-diaminonaphthalenepalladium(II) complex in 46.0% yield. Palladium analysis for PdC₁₂H₁₀N₄S₂: Calculated, 27.94%; Found, 23.92%.

The infrared spectrum for this product showed a band at 2100 cm⁻¹, assigned to $\nu_{CN}$; a band at 415 cm⁻¹, assigned to $\delta_{NCN}$; and a band at 710 cm⁻¹, 1 assigned to $\nu_{CS}$.

COMPARATIVE EXAMPLE E

Bis(Thiocyanato)diaminoacetonepalladium(II)

Potassium tetrachloropalladate (0.326 g, 1 mmole) was dissolved in water (5 ml) and solid potassium thiocyanate (0.390 g, 4 mmoles) was added. A red solution was obtained and after filtering off a small amount of insoluble material, a solution of diaminoacetone dihydrobromide (0.25 g, 1 mmole) in water (10 ml) was added. The addition of 1M sodium hydroxide (2 ml) resulted in the formation of a precipitate and this material was filtered, washed with water and alcohol and vacuum dried to afford 0.23 (74.1% of bis(thiocyanato)-diaminoacetone-palladium(II).

| Analysis for PdC₅H₈N₄OS₂: | | | |
|---|---|---|---|
| | % C | % H | % N |
| Calculated: | 19.33 | 2.60 | 18.03 |
| Found: | 19.90 | 1.93 | 18.91 |

The infrared spectrum for this product showed a band at 210 cm⁻¹, assigned to $\nu_{CN}$; a band at 415 cm⁻¹, assigned to $\delta_{NCN}$; and a band at 710 cm⁻¹, assigned to $\nu_{CS}$.

COMPARATIVE EXAMPLES F–I

Dinitro(Ethylenediamine)palladium(II)

Sodium tetrachloropalladate (1.47 g, 5 mmoles) was dissolved in water (50 ml) and a solution of sodium nitrite (1.38 g, 20 mmoles) in water (10 ml) was added. A light yellow color formed immediately, and to this solution was added a solution of ethylenediamine (0.30 g, 5 mmoles). The mixture was stirred at room temperature for 30 minutes and then cooled in a refrigerator for one hour. The yellow product was filtered, washed with water and ethanol and vacuum dried. There was thus obtained 0.92 g (71.2% yield) of dinitro(ethylenediamine)palladium(II). Palladium anaylsis: Calculated, 41.16%; Found, 41.90%.

The procedure of this Comparative Example was repeated, except that 1,3-diaminopropane, 1,2-diaminocyclohexane and o-phenylenediamine were substituted for the ethylenediamine therein described. There were thus obtained dinitro(1,3-diaminopropane)-palladium(II), dinitro(1,2-diaminocyclohexane)-palladium(II) and dinitro(o-phenylenediamine)palladium(II).

Dinitro(1,3-diaminopropane)palladium(II) (yield: 55.8%). Palladium analysis: Calculated, 39.04%; Found, 39.44%.

Dinitro(1,2-diaminocyclohexane)palladium(II) (yield: 85.1%). Palladium analysis: Calculated, 34.03%; Found, 32.95%.

Dinitro(o-phenylenediamine)palladium(II) (yield: 75.7%). Palladium analysis: Calculated, 34.71%; Found 34.57%.

COMPARATIVE EXAMPLES J-K

Dicyano(ethylenediamine)palladium(II)

Palladous cyanide [Pd(CN)$_2$.x4$_2$O] (1.0 g) was suspended in water (1 ml) and ethylenediamine (1.0 g) was added. The mixture was warmed gently on a steam bath until all of the palladous cyanide dissolved. Upon cooling in a refrigerator for one hour, the product was obtained in the form of white needles. This product was filtered, washed with water and ethanol and vacuum dried to afford 0.33 g of dicyano(ethylenediamine)-palladium(II).

Dicyano(1,2-diaminocyclohexane)palladium(II) was prepared in an essentially identical manner by substituting 1,2-diaminocyclohexane for the ethylenediamine in the preceding method, and otherwise following the procedure therein described.

COMPARATIVE EXAMPLE L

Diiodo(ethylenediamine)palladium(II)

Potassium iodide (1.66 g, 10 mmoles) was dissolved in water (20 ml) and sodium tetrachloropalladate (0.294 g, 1 mmole) was added. The resulting mixture produced a black solid. A solution of ethylenediamine (0.060 g, 1 mmole) in water (2 ml) was added to this mixture, and it was stirred at room temperature for 15 minutes. The black solid eventually dissolved and a yellow-brown precipitate formed. This precitate was filtered, washed with water and ethanol and vacuum dried. The resulting diiodo(ethylenediamine)palladium(II) was obtained in 50% yield (0.21 g).

COMPARATIVE EXAMPLE M

Diiodo(1,2-Diaminocyclohexane)palladium(II)

Dichloro(1,2-diaminocyclohexane)palladium(II) (0.291 g, 1 mmole) was suspended in water (30 ml) and solid potassium iodide (0.332 g, 2 mmoles) was added. The mixture was warmed briefly to about 60° C. and then stirred at room temperature overnight. The resulting brown solid was filtered, washed with water and ethanol and vacuum dried to afford 0.30 g (63.6%) of diiodo(1,2-diaminocyclohexane)palladium(II).

ANTI-TUMOR EVALUATION

The above-prepared compounds were evaluated against S180 ascites in female CFW Swiss mice. The mice were weighed (average weight: 20 g), placed into cages (four or six mice to a cage), and on day zero the mice were inoculated with 0.2 ml of a freshly prepared saline suspension (0.15 M NaCl) containing $1 \times 10^7$ tumor cells/ml or a total of $2 \times 10^6$ cells This inoculum was freshly prepared using "transfer" mice, which had been injected with tumor cells the previous week; it was obtained via the following steps: (1) the removal of cells from the peritoneal cavity of the sacrificed transfer mouse, (2) alternate centrifugation and washing operations (2-3 times with cold saline) to remove blood and other components, and (3) dilution of the volume of the packed cell with saline (1:3). A final centrifugation was carried out at 1000 RPM over a two minute period. A cell count was made on a 2,000-fold dilution of this 1:3 suspension by means of a Coulter Counter. A final dilution to $1 \times 10^7$ cells/ml was made, based on the average count.

On day 1, solutions of the test compounds were prepared, and each mouse in a set of four or six were injected with the same test compound at the same dosage. The doses were based on the average weight of the animals (cage weight). Also, beginning on day 1, two controls were employed containing six mice per control:

(1) Normal Control: This consisted solely of the carrier or diluent used in combination with the test compound; and (2) Positive Control: This consisted solely of known anti-tumor agent cis-[Pt(NH$_3$)$_2$Cl$_2$] in saline (8 mg/kg) to test the response of the biological system.

The effectiveness of a test compound was measured in terms of the % increase in life span (%ILS) of the test mice relative to the Normal Control (Calculated from the day of tumor inoculation, i.e., day zero). To standardize the test data and permit intercomparisons, the day of evaluation was arbitrarily taken as that day corresponding to twice the mean life span (or average day of death) of the control. This established a practical upper limit of 100% on the %ILS attainable. For calculation purposes, the survivors of the day of evaluation were considered to have died on that day. The %ILS was calculated as follows:

$$\% \text{ILS} = \left( \frac{\text{mean-life span of test mice}}{\text{mean-life span of control mice}} - 1 \right) \times 100\%$$

ILS values in excess of 50% were interpreted as antitumor activity, whereas values in excess of 75% indicated excellent antitumor activity.

All test compounds were evaluated in water containing 0.1–0.3% of the suspending agent "Klucel" (hydroxypropylcellulose). The results of these tests are shown in Table 2:

TABLE 2

Bis-Thiocyanato—Pd Complexes; Five Membered Rings Anti-Tumor Screening Data; S 180 Ascites

| Example; (Amine) | Dose (mg/kg) | % ILS | Survivors | Positive Control % ILS | Survivors |
|---|---|---|---|---|---|
| Ex. 1 (Ethylenediamine) | 10 | 2 | 0 of 4 | 74 | 2 of 6 |
|  | 20 | 18 | 0 of 4 |  |  |
|  | 40 | 79 | 0 of 4 |  |  |
|  | 80 | 2 | 1 of 4 |  |  |
|  | 160 | −87 | 0 of 4 |  |  |
|  | 320 | −87 | 0 of 4 |  |  |
| Ex. 2 (1,2-Diaminopropane) | 5 | 16 | 0 of 6 | 87 | 2 of 6 |
|  | 10 | 13 | 0 of 6 |  |  |
|  | 20 | 17 | 0 of 6 |  |  |
|  | 40 | 59 | 2 of 6 |  |  |
|  | 80 | −21 | 1 of 6 |  |  |
|  | 160 | −74 | 0 of 6 |  |  |
| Ex. 3 (1,2-Diaminocyclohexane) | 5 | 0 | 0 of 4 | 95 | 3 of 6 |
|  | 10 | 5 | 0 of 4 |  |  |
|  | 20 | 1 | 0 of 4 |  |  |
|  | 40 | −1 | 0 of 4 |  |  |
|  | 80 | 75 | 3 of 4 |  |  |
|  | 160 | 39 | 1 of 4 |  |  |
|  | 40 | −3 | 0 of 4 | 87 | 1 of 4 |
|  | 60 | 22 | 0 of 4 |  |  |
|  | 80 | 100 | 4 of 4 |  |  |
|  | 100 | 79 | 2 of 4 |  |  |
|  | 120 | 36 | 2 of 4 |  |  |
|  | 140 | 36 | 1 of 4 |  |  |
| Ex. 4. (N,N'Dimethylethylenediamine) | 5 | −2 | 0 of 6 | 73 | 3 of 6 |
|  | 10 | 1 | 0 of 6 |  |  |
|  | 20 | −5 | 0 of 6 |  |  |
|  | 40 | 18 | 1 of 6 |  |  |

TABLE 2-continued

Bis-Thiocyanato—Pd Complexes; Five Membered Rings
Anti-Tumor Screening Data; S 180 Ascites

| Example; (Amine) | Dose (mg/kg) | % ILS | Sur-vivors | Positive Control % ILS | Positive Control Survivors |
|---|---|---|---|---|---|
| | 80 | 62 | 2 of 6 | | |
| | 160 | −45 | 1 of 6 | | |
| Ex. 5. (o-Phenylene-diamine) | 10 | 14 | 0 of 4 | 89 | 2 of 6 |
| | 20 | 15 | 0 of 4 | | |
| | 40 | 27 | 0 of 4 | | |
| | 80 | 81 | 2 of 4 | | |
| | 160 | 79 | 1 of 4 | | |
| | 320 | −73 | 0 of 4 | | |
| Ex. 6. (4,5-Dimethyl-o-phenylene-diamine) | 5 | −1 | 0 of 6 | 87 | 2 of 6 |
| | 10 | 24 | 0 of 6 | | |
| | 20 | 10 | 0 of 6 | | |
| | 40 | 2 | 0 of 6 | | |
| | 80 | 13 | 0 of 6 | | |
| | 160 | 65 | 2 of 6 | | |

Table 2 indicates that bis(thiocyanato)palladium(II) complexes containing both bidentate amine ligands and a 5-numbered ring are effective in the treatment of S180 ascites.

Tables 3 and 4, infra, show the criticality of the ring size and the thiocyanato substituents, respectively. The protocols for determining effectiveness for the products in Tables 3 and 4 were identical to the procedure employed for determining the anti-tumor effectiveness of the products in Table 2.

TABLE 3

Bis-Thiocyanato—Pd Complexes; Six and Seven Membered Rings
Anti-Tumor Screening Data; S 180 Ascites

| Amine (Procedure/Example) | Dose (mg/kg) | % ILS | Sur-vivors | Positive Control % ILS | Positive Control Survivors |
|---|---|---|---|---|---|
| 1,8-Diamino-naphthalene; (Comp. Ex. D) | 10 | −11 | 0 of 6 | 65 | 1 of 6 |
| | 20 | −9 | 0 of 6 | | |
| | 40 | −11 | 0 of 6 | | |
| | 80 | −19 | 0 of 6 | | |
| | 160 | −28 | 0 of 6 | | |
| | 320 | 48 | 1 of 6 | | |
| 1,4-Diamino-butane; (Comp. Ex. B) | 10 | −1 | 0 of 6 | 65 | 1 of 6 |
| | 20 | 15 | 0 of 6 | | |
| | 40 | −4 | 0 of 6 | | |
| | 80 | −21 | 0 of 5 | | |
| | 160 | 47 | 0 of 5 | | |
| | 320 | 2 | 0 of 5 | | |
| Diaminoacetone; (Comp. Ex. E) | 5 | 3 | 0 of 4 | 95 | 3 of 6 |
| | 10 | 8 | 0 of 4 | | |
| | 20 | 13 | 0 of 4 | | |
| | 40 | 3 | 0 of 4 | | |
| | 80 | 1 | 0 of 4 | | |
| | 160 | 13 | 0 of 4 | | |
| 1,3-Diamino-propane; (Comp. Ex. A) | 10 | 1 | 0 of 4 | 89 | 2 of 6 |
| | 20 | 9 | 0 of 4 | | |
| | 40 | −4 | 0 of 4 | | |
| | 80 | −70 | 0 of 4 | | |
| | 160 | −88 | 0 of 4 | | |
| | 320 | −93 | 0 of 4 | | |
| 1,3-Diamino-2-propanol; (Comp. Ex. C) | 10 | −4 | 0 of 6 | 76 | 1 of 6 |
| | 20 | −7 | 0 of 6 | | |
| | 40 | −8 | 0 of 6 | | |
| | 80 | −76 | 0 of 6 | | |
| | 160 | −87 | 0 of 6 | | |
| | 320 | −92 | 0 of 6 | | |

On the basis of the foregoing data, it can be concluded that bis(thiocyanato)palladium(II) complexes containing 6- and 7-membered chelate rings are essentially inactive.

The effect of hte thiocyanato radical on anti-tumor activity is illustrated by comparing the data in Table 2 with the data in Table 4.

TABLE 4

Nitro, Cyano and Iodo—Pd Complexes
Anti-Tumor Screening Data; S 180 Ascites

| Complex (Procedure/Example) | Dose (mg/kg) | % ILS | Sur-vivors | % ILS | Sur-vivors |
|---|---|---|---|---|---|
| Dinitro(1,3-Diamino-propane)palladium(II); (Comp. Ex. G) | 10 | 13 | 0 of 4 | 88 | 3 of 6 |
| | 20 | 16 | 0 of 4 | | |
| | 40 | 27 | 0 of 4 | | |
| | 80 | 0 | 1 of 4 | | |
| | 160 | −89 | 0 of 4 | | |
| Dinitro(o-phenylene-diamine)palladium(II); (Comp. Ex. I) | 10 | 21 | 0 of 4 | 83 | 1 of 6 |
| | 20 | 3 | 0 of 4 | | |
| | 40 | 29 | 1 of 4 | | |
| | 80 | 19 | 0 of 4 | | |
| Dinitro(1,2-Diamino-cyclohexane)palladium-(II); (Comp. Ex. H) | 10 | 12 | 0 of 4 | 83 | 1 of 6 |
| | 20 | 3 | 0 of 4 | | |
| | 40 | −3 | 0 of 4 | | |
| | 80 | 21 | 0 of 4 | | |
| Dinitro(ethylene-diamine)palladium(II); (Comp. Ex. F) | 10 | 2 | 0 of 4 | 88 | 3 of 6 |
| | 20 | 6 | 0 of 4 | | |
| | 40 | −15 | 0 of 4 | | |
| | 80 | −59 | 0 of 4 | | |
| | 160 | −87 | 0 of 4 | | |
| Dicyano(ethylene-diamine)palladium(II); (Comp. Ex. J) | 5 | −1 | 0 of 4 | 54 | 0 of 6 |
| | 10 | 6 | 0 of 4 | | |
| | 20 | 15 | 0 of 4 | | |
| | 40 | 2 | 0 of 4 | | |
| | 80 | 38 | 0 of 4 | | |
| | 160 | −94 | 0 of 4 | | |
| Dicyano(1,2-Diamino-cyclohexane)palladium-(II); (Comp. Ex. K) | 5 | 18 | 1 of 4 | 54 | 0 of 6 |
| | 10 | 25 | 0 of 4 | | |
| | 20 | 17 | 0 of 4 | | |
| | 40 | −81 | 0 of 4 | | |
| | 80 | −81 | 0 of 4 | | |
| | 160 | −94 | 0 of 4 | | |
| Diiodo(ethylene-diamine)-palladium(II); (Comp. Ex. L) | 5 | −17 | 0 of 4 | 49 | 1 of 6 |
| | 10 | −13 | 0 of 4 | | |
| | 20 | −9 | 0 of 4 | | |
| | 40 | −11 | 0 of 4 | | |
| | 80 | 24 | 0 of 4 | | |
| | 160 | 32 | 1 of 4 | | |
| Diiodo(1,2-Diamino-cyclohexane)palladium-(II); (Comp. Ex. M) | 5 | −4 | 0 of 4 | 49 | 1 of 6 |
| | 10 | −9 | 0 of 4 | | |
| | 20 | −20 | 0 of 4 | | |
| | 40 | −15 | 0 of 4 | | |
| | 80 | −16 | 0 of 4 | | |
| | 160 | 77 | 1 of 4 | | |

On the basis of the data in Table 4, it can be concluded that the thiocyanato radical is critical to the structure of the present complexes (I) and that the substitution of nitro, cyano and iodo for thiocyanato actually serves to inhibit anti-tumor effectiveness.

The effective dose ($ED_{90}$), lethal does ($LD_{50}$) and therapeutic index (TI) were determined, via the method of Miller and Taiter (Reported by R. A. Turner, "Screening Methods in Pharmacology", Academic Press, New York, pages 61–62 (1976)).

The results of this test are shown in Table 5. In this study, $ED_{90}$ represents the dose which causes a 50% increase in life span (ILS) in 90% of the test animals (mice), determined graphically. The $LD_{50}$ value represents the lethal dose in 50% of said animals.

TABLE 5

Anti-Tumor Screening Data for
Bis(Thiocyanato)Palladium Complexes; S180 Ascites

| Example (Amine) | Best % ILS | $ED_{90}$ | $LD_{50}$ | Therapeutic Index |
|---|---|---|---|---|
| Ex. 1. (Ethylene-diamine) | 79 | 38 | 80 | 2.1 |
| Ex. 2. (1,2-Diamino propane) | 59 | — | 76 | — |
| Ex. 3. | 100 | 78 | 160 | 2.0 |
| (1,2-Diamino- | 75 | 97 | 270 | 2.8 |

TABLE 5-continued

| Anti-Tumor Screening Data for Bis(Thiocyanato)Palladium Complexes; S180 Ascites | | | | |
|---|---|---|---|---|
| Example (Amine) | Best % ILS | $ED_{90}$ | $LD_{50}$ | Therapeutic Index |
| cyclohexane) | | | | |
| Ex. 4. (N,N'Dimethyl-ethylenediamine) | 62 | 100 | 120 | 1.2 |
| Ex. 5. (o-Phenylene-diamine) | 81 | 130 | 230 | 1.8 |
| Ex. 6. (4,5-Dimethyl-o-phenylenediamine) | 65 | 200 | 360 | 1.8 |

This table indicates that all complexes (I) where data is available possess favorable therapeutic indexes.

The palladium(II) products (I) herein-described are merely illustrative of the invention and they are capable of wide variation and modification. Alterations to these products are within the skill of the artisan to effect and, therefore, derivatives which prove to be similarly useful are also considered to be within the scope of this invention.

What is claimed is:

1. A pharmaceutical composition for treating malignant animal tumor cells sensitive to a compound of the formula:

$$\begin{array}{c} R^1 \quad R^6 \\ | \quad | \\ R^2-C^*-NH \qquad SCN \\ \qquad \qquad \backslash \quad / \\ \qquad \qquad Pd \\ \qquad \qquad / \quad \backslash \\ R^3-C^*-NH \qquad SCN \\ | \quad | \\ R^4 \quad R^5 \end{array}$$

comprising as the active ingredient a therapeutically effective amount for treatment of said tumor cells of said compound of the formula:

$$\begin{array}{c} R^1 \quad R^6 \\ | \quad | \\ R^2-C^*-NH \qquad SCN \\ \qquad \qquad \backslash \quad / \\ \qquad \qquad Pd \\ \qquad \qquad / \quad \backslash \\ R^3-C^*-NH \qquad SCN \\ | \quad | \\ R^4 \quad R^5 \end{array}$$

wherein $R^1$ and $R^4$ are hydrogen or $C_{1-6}$ alkyl;

$R^2$ and $R^3$ are hydrogen, $C_{1-6}$ alkyl, hydroxymethyl or, taken together, $R^2$ and $R^3$ represent $C_{2-6}$ alkylene;

$R^1$-$R^4$, taken together with the carbon atoms to which they are attached, represent naphtylene or a phenylene of the formula:

$$\begin{array}{c} CH \\ HC \diagup \diagdown C^*- \\ \| \quad | \\ R^7-C \quad C^*- \\ \diagdown \diagup \\ C \\ | \\ R^8 \end{array}$$

wherein $R^7$ and $R^8$ represent hydrogen, $C_{1-6}$ alkyl, hydroxy or carboxy; and $R^5$ and $R^6$ are hydrogen, $C_{1-6}$ alkyl, hydroxymethyl or carboxymethyl in combination with a non-toxic pharmacologically acceptable inert carrier or diluent.

2. The composition according to claim 1, wherein $R^1$ and $R^4$ each represent hydrogen;

$R^2$ and $R^3$ are selected from the group consisting of hydrogen, $C_{1-6}$ alkyl and, taken together, $R^2$ and $R^3$ represent lower alkylene containing from about 3-5 carbon atoms;

$R^1$-$R^4$, taken together with the carbon atoms to which they are attached, represent a phenylene of the formula:

$$\begin{array}{c} CH \\ HC \diagup \diagdown C^*- \\ \| \quad | \\ R^7-C \quad C^*- \\ \diagdown \diagup \\ C \\ | \\ R^8 \end{array}$$

wherein $R^7$ and $R^8$ represent hydrogen or $C_{1-6}$ alkyl; and $R^5$ and $R^6$ are selected from the group consisting of hydrogen and $C_{1-6}$ alkyl.

3. The composition according to claim 2, wherein $R^2$ and $R^3$ may be the same or different and represent hydrogen or $C_{1-6}$ alkyl.

4. The composition according to claim 3, wherein $R^2$ and $R^3$ represent hydrogen or methyl.

5. The composition according to claim 4, wherein $R^2$ and $R^3$ taken together, represent a lower alkylene containing from about 3-5 carbon atoms.

6. The composition according to claim 5, wherein $R^2$ and $R^3$, taken together, represent butylene.

7. The composition according to claim 2, wherein $R^1$-$R^4$, taken together with the carbon atoms to which they are attached, represent a phenylene of the formula:

$$\begin{array}{c} CH \\ HC \diagup \diagdown C^*- \\ \| \quad | \\ R^7-C \quad C^*- \\ \diagdown \diagup \\ C \\ | \\ R^8 \end{array}$$

wherein $R^7$ and $R^8$ represent hydrogen or $C_{1-6}$ alkyl.

8. The composition according to claim 7, wherein $R^7$ and $R^8$ represent methyl.

9. The composition of claim 1 in a form suitable for parenteral administration.

10. The composition of claim 1 in a form suitable for oral administration.

11. The composition of claim 10 in tablet form.

12. The composition of claim 10 in capsule form.

13. The composition of claim 1 wherein the compound is the active ingredient and it is present in an amount of from about 5 to 400 mg.

14. A method of treating malignant animal tumor cells sensitive to a compound of the formula:

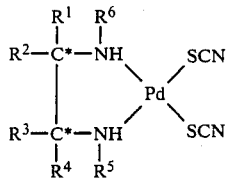

wherein $R^1$ and $R^4$ are hydrogen or $C_{1-6}$ alkyl;

$R^2$ and $R^3$ are hydrogen, $C_{1-6}$ alkyl, hydroxymethyl or, taken together, $R^2$ and $R^3$ represent $C_{2-6}$ alkylene;

$R^1$-$R^4$, taken together with the carbon atoms to which they are attached, represent naphtylene or a phenylene of the formula:

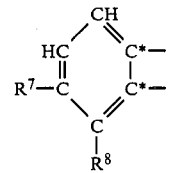

wherein $R^7$ and $R^8$ represent hydrogen, $C_{1-6}$ alkyl, hydroxy or carboxy; and $R^5$ and $R^6$ are hydrogen, $C_{1-6}$ alkyl, hydroxymethyl or carboxymethyl which comprises administering said compound, or a mixture of said compounds, to an animal afflicted with said tumor cells in an amount sufficient to cause regression of same.

15. The method according to claim 14 wherein said compound is administered in a single dose.

16. The method of claim 14 wherein said compound is administered in multiple doses.

17. The method of claim 14 wherein said compound is administered parenterally.

18. The method of claim 14 wherein said compound is administered orally.

19. The method of claim 14, wherein said compound is administered in the form of a composition together with a pharmaceutically acceptable carrier or diluent.

* * * * *